United States Patent [19]
Follett

[11] Patent Number: 5,053,625
[45] Date of Patent: Oct. 1, 1991

[54] SURFACE CHARACTERIZATION APPARATUS AND METHOD

[75] Inventor: Gary J. Follett, St. Paul, Minn.

[73] Assignee: Minnesota Mining and Manufacturing Company, St. Paul, Minn.

[21] Appl. No.: 606,530

[22] Filed: Oct. 31, 1990

Related U.S. Application Data

[62] Division of Ser. No. 228,396, Aug. 4, 1988, Pat. No. 5,001,939.

[51] Int. Cl.$^5$ .................. H01J 37/305; G01F 1/37
[52] U.S. Cl. ................... 250/440.1; 250/441.1; 250/442.1; 250/400; 250/492.1; 250/304; 250/305
[58] Field of Search ............ 250/440.1, 441.1, 442.1, 250/310, 453.1, 455.1, 304, 305, 398, 400, 492.1; 73/864.81, 863; 414/217; 118/712, 719; 427/8; 204/192.13

[56] References Cited

U.S. PATENT DOCUMENTS

| | | | |
|---|---|---|---|
| 2,640,788 | 6/1953 | Rockett, Jr. | 117/33.25 |
| 3,104,321 | 9/1963 | Smith, Jr. | 250/400 |
| 3,294,670 | 12/1966 | Charschan et al. | 204/298 |
| 3,805,736 | 4/1974 | Foehring et al. | 118/49 |
| 4,015,558 | 4/1977 | Small et al. | 118/6 |
| 4,348,886 | 9/1982 | Faith, Jr. | 73/19 |
| 4,400,409 | 8/1983 | Izu et al. | 427/39 |
| 4,410,558 | 10/1983 | Izu et al. | 427/39 |
| 4,438,723 | 3/1984 | Cannellar et al. | 118/719 |
| 4,442,788 | 4/1984 | Weis | 118/405 |
| 4,642,467 | 2/1987 | Yamawaki et al. | 250/400 |
| 4,732,776 | 3/1988 | Boissevain | 427/10 |
| 4,810,342 | 3/1989 | Inoue | 204/192.17 |
| 4,841,908 | 6/1989 | Jacobson et al. | 118/718 |
| 4,874,631 | 10/1989 | Jacobson et al. | 427/39 |
| 4,985,635 | 1/1991 | Inokuti et al. | 250/492.1 |

FOREIGN PATENT DOCUMENTS 0041773 12/1981 European Patent Office .
3247831 7/1983 Fed. Rep. of Germany .
58-189371 11/1983 Japan .

OTHER PUBLICATIONS

A: Hercules, *Analytical Chemistry*, 58(12), 1177–1190 (Oct. 1986).
B: Zalar, *Thin Solid Films*, 124, 223–230 (1985).
C: Zalar, *Surface and Interface Analysis*, 9, 41–46 (1986).
D: Bodo et al., *J. Vac. Sci. Technol. A.*, 2(4), 1498–1502 (Oct.–Dec. 1984).
E: Bodo et al., *Surface and Interface Analysis*, 9, 437–440 (1986).
F: Ho et al., *J. Vac. Sci. Technol. A.*, 3(3), 739–745 (May/Jun. 1985).
G: Chou et al., *J. Vac. Sci. Technol. A.*, 2(2), 751–755 (Apr.–Jun. 1984).
H: Stroh et al., *LC-GC*, 5(7), 562–570 (Jul. 1987).

Primary Examiner—Jack I. Berman
Assistant Examiner—Kiet T. Nguyen
Attorney, Agent, or Firm—Merchant, Gould, Smith, Edell, Welter & Schmidt

[57] ABSTRACT

An apparatus for conducting surface characterizations of sample materials comprises an enclosure defining first and second substantially isolated operating chambers or regions. The operating regions are separated by narrow channels, and are preferably differentially pumped. An elongate substrate extends between the first and second regions. During operation, a sample surface to be studied is prepared on the substrate in the first region, is transported into the second region, and is analyzed thereat. In a preferred embodiment a continuous loop and pulley arrangement is provided, for the substrate. Also, for a preferred embodiment the first region is divided into first and second isolated chambers, through which the substrate is extended. A method is provided, whereby a surface can be prepared and analyzed. According to the method, the sample is applied to a substrate in a first region, and the substrate is transported into a second isolated region, through an elongate narrow channel. Differential pumping facilitates isolation of environments in the various regions.

17 Claims, 4 Drawing Sheets

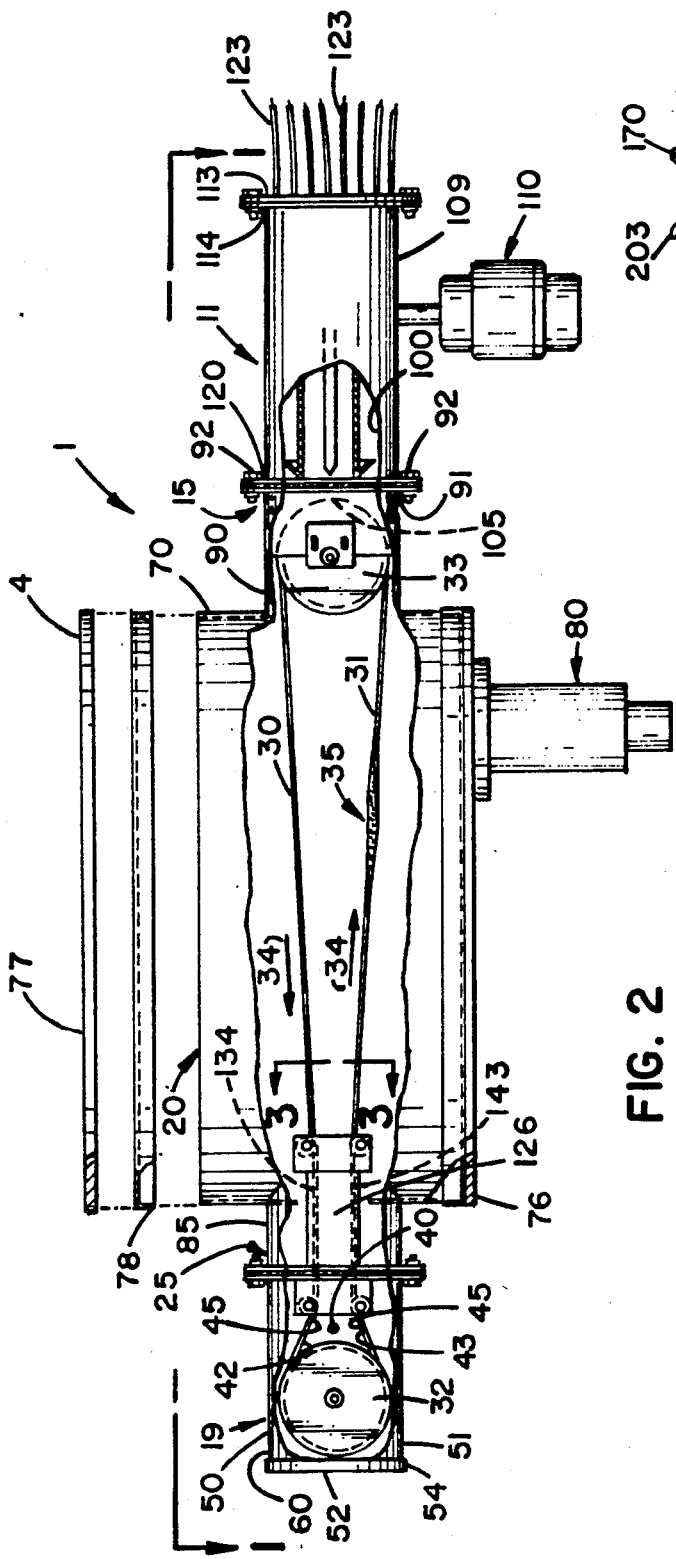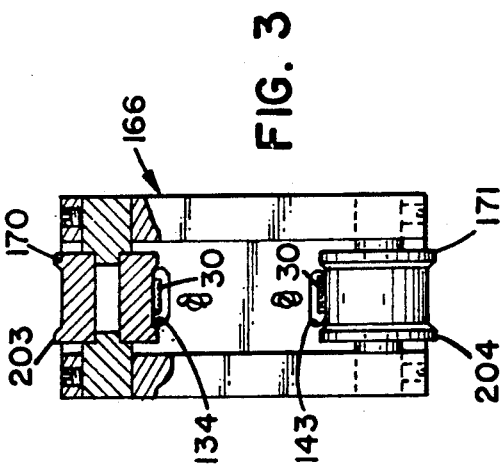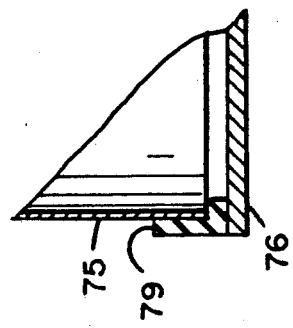

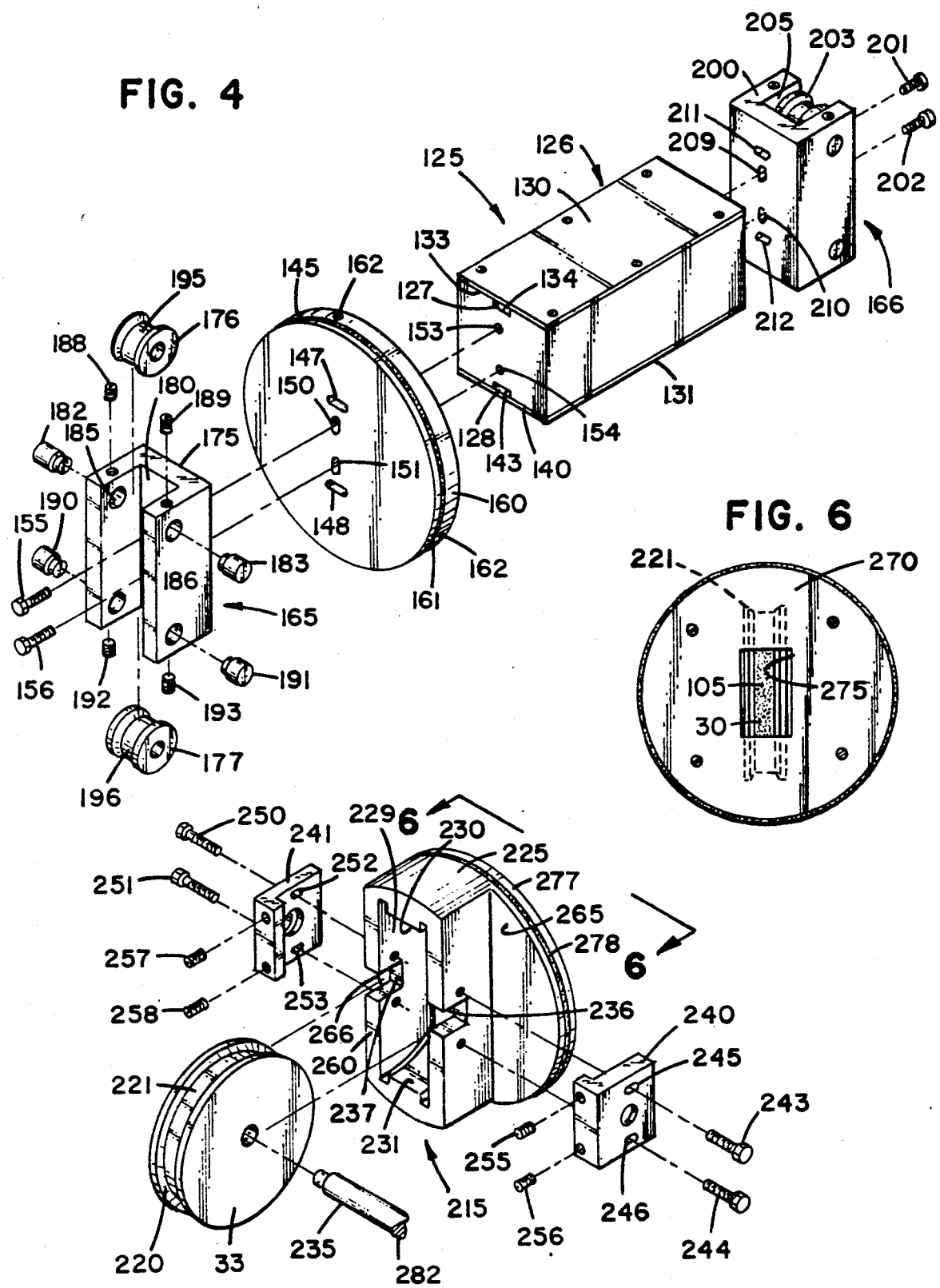

SURFACE CHARACTERIZATION APPARATUS AND METHOD

CROSS REFERENCE TO RELATED APPLICATION

The present application is a Division of U.S. Ser. No. 07/228,396, filed Aug. 4, 1988, which issued as U.S. Pat. No. 5,001,939 on Mar. 26, 1991.

FIELD OF THE INVENTION

The present invention concerns surface analysis techniques and devices, and in particular arrangements for use in association with analytical instruments or the like. The invention particularly concerns an arrangement and method for advantageously presenting a film surface to an analytical device, such as a surface probe of an Auger electron spectroscopic device, for analysis.

BACKGROUND OF THE INVENTION

To enhance an understanding of the physical and chemical characteristics of a wide variety of materials, surface analyses are often conducted. Typically, surface analysis techniques involve the characterization of the top 1.0–50.0 angstroms (Å) of a solid. Although many techniques can be, and have been, used for surface characterization, four techniques have generally predominated. These are: X-Ray photoelectron spectroscopy (ESCA); Auger electron spectroscopy (AES); secondary ion mass spectroscopy (SIMS); and, low energy ion scattering spectrometry (ISS). These techniques are discussed briefly in: Hercules, D. M., *Analytical Chemistry of Surfaces*, Volume 58, No. 12, October 1986, page 1177–1190, incorporated herein by reference.

Generally, the application of highly sensitive spectroscopic or spectrometric techniques are subject to operational limitations when applied to surface analyses. The surface being tested may be subject to interference by adventitious species. For example, water, hydrocarbons, fine dust particles etc. can become absorbed or adsorbed onto the surface being characterized, and interfere with the analysis. Also, damage, for example heat damage, to the surface being analyzed, for example by the spectroscopic probe, can introduce errors and/or artificial limitations. Further, if the surface being analyzed involves relatively short-lived species, decomposition or deterioration of the surface, prior to completion of analysis, can cause problems. This is a particular problem, for conventional systems, if the sample has to be transported from a location of preparation to an analysis lab.

Various techniques have been developed, to address some, or all, of the above concerns. Generally these have revolved around application of a variety of general methods, including: methods for cleaning a prepared sample surface prior to analysis; neutralizing surface charge to minimize errors in spectroscopy introduced by surface charge; and, methods for reduction of sample heating effects during analysis. Conventional cleaning techniques include sputter etching and sample heating to desorb contaminants. Conventional methods for reduction of heating effects include sample cooling and modifications of the excitation beam or probe.

Sputter etching is a well-known method of generating a clean surface, whereby a cathode, in vacuum, is energized to generate ions in the gas phase which impinge on the sputtered (sample) surface. This etches or cleans the sample surface. Sputter etching of a sample prior to analysis can effectively produce a surface without adventitious species. However, differential sputtering effects can cause a change in a composition of the test sample. Further, substantial undesired mixing effects of layers of the sample by knock-in can be brought about. In addition, the chemical reactivity of the surface of the sample may be affected. Also, without follow-up protection the surface may become damaged or contaminated.

Heating to remove volatile surface contaminants, prior to analysis, is helpful in some applications. However, some samples are not sufficiently thermally stable to withstand such treatments. Also, some surface contaminants are not sufficiently volatile to be easily removed by such techniques.

Surface neutralization techniques involve the bombardment of the sample surface with low energy electrons, to counteract any surface charges and enhance the analysis. In particular, this technique reduces spectral errors in charged particle spectroscopies. The technique, however, is often accompanied by inhomogeneous charging and subsequent spectral peak broadening, and thus is not completely effective. Techniques for measurement of surface charge, with correction for charging effects, require an assumption of uniform positive charging, and thus inherently involve limitations.

Sample cooling, to offset probe damage, has been somewhat effective in enhancing surface analyses. However, this technique requires a good thermal conductivity of the sample and a thermal contact to the cooling mechanism. In complicated, moderate to high vacuum arrangements, this may be difficult or expensive to achieve. Also, sample cooling may increase adsorption onto the sample surface of residual contaminants in the vacuum system.

Beam and probe modifications of certain surface analytical instruments, to achieve improvements, are also taught in the art. Beam filtering, for example, reduces X-ray damage in XPS, but it also severely reduces X-ray flux. Thus, a poorer signal to noise ratio results, and longer data acquisition time is necessitated. This can be a particular problem with short-lived films. Beam rastering and defocussing in AES has decreased, but has not eliminated, damage effects to the sample by diminishing the residence time of the beam on any particular sample spot or location.

When moderate to highly reactive sample surfaces are involved, for example a freshly deposited aluminum film, rapid contamination from residuals in the chamber will likely result, unless the sample is continuously maintained in ultra-high vacuum (approx. $10^{-10}$ torr.). Such a vacuum may be difficult to obtain and maintain in some systems, for example most vacuum deposition systems cannot readily achieve such low pressures. Also, the vapor pressures of same samples are too high to permit such a vacuum. Thus, it is desired, in many instances, that the sample be quickly removed from an environment of preparation or contamination, after generation. However, conventional methods and apparatuses have not readily accommodated this. Generally, problems have concerned: maintenance of selected temperature, pressure and atmosphere; movement without substantial risk of surface damage; and, movement within a selected and preferably precisely controlled period of time.

At least one area in which sample movement systems have been developed for use in association with analytical devices is the field of providing for sample rotation to achieve an averaging in spectra. For example, a sample holder with a special mechanism enabling sample rotation during depth analysis by AES is described in: Zalar, A., Thin Solid Films, Volume 124, page 223–230 (1985) and Surface and Interface Analysis, Volume 9, page 41–46 (1986) incorporated herein by reference. Such sample handling systems do not readily lend assistance to the above described problems, since movement between regions of controlled, and often different, pressures, atmospheres and temperature are not readily achievable with them.

In general, what has been needed has been an apparatus and method for surface characterization which achieves improvement through a reduction in, and preferably a minimization of, undesirable effects such as surface contamination and damage. Preferably, a system which readily accommodates the necessary and desirable temperature and pres. ⟶ r⟶ ⟶equ ⟶ ⟶m⟶nts for sample preparation, handling an ⟶ ⟶aracterization has been needed.

SUMMARY OF THE INVENTION

According to the present invention, a method for surface characterization generally comprises preparation of the surface sample to be tested in a first sample region, and isolation and testing of the surface in a second sample region. Transport of the sample between the first region and the second region, in a relatively short period of time, facilitates the operation. Preferably, the regions are substantially isolated volumes; and, means facilitating maintenance of the isolated regions under different pressures, atmospheric content and temperature, to facilitate the different processes conducted in the two regions. This is accomplished, in general, through provision of an elongate transport channel arrangement extending between and in communication with the isolated regions. Different environments in the isolated regions are obtainable with application of differential pumping techniques. Means facilitating preferred, selected, and, if desired, relatively rapid removal of a prepared surface from the first region to the second is provided. As a result, the sample is rapidly isolated from the region of formation, before substantial surface contamination or damage can occur. Thus, a method according to the present invention generally comprises: providing first and second substantially isolated regions having a narrow passageway or channel extending therebetween; preparing a sample to be studied in the first region on a substrate which extends through the passage way; transporting the sample to the second region, generally by transport through the channel; and, evaluating the sample by analytical processes conducted in the second region. Preferably, an apparatus facilitating a surface analysis conducted according to the method comprises: an enclosure defining first and second isolated regions; seal means substantially isolating the first and second regions from one another, the seal means including an elongate transport channel arrangement extending between and in communication with the first and second regions; and, a sample transport mechanism constructed and arranged to transport the sample from the first region through the transport channel arrangement to the second region. Preferably, a pump mechanism is provided in an operative communication with the first and second regions, to facilitate differential pumping and provision of different environments therein. Typically, differential ⟶ping will be provided by a pump mechanism comprising independent pumps in communication with one each of the regions.

For many experiments, it will be desired to provide at least two isolated volumes in the first region, to accommodate sample preparation procedures which are facilitated by steps undertaken in different chemical and/or physical environments. To accommodate this, in preferred applications the sample to be tested is moved through regions involving at least three chambers: a first chamber in which initial preparation steps for a surface to be analyzed are conducted; a second chamber in which further steps of sample preparation can be conducted, or which can serve as an isolation chamber in which the sample can be maintained removed from contaminating species in the first chamber; and, a third chamber, comprising the second region, in which the probe for conducting an analytical process is positioned. For typical processes, the three chambers are maintained under different pressures and the sample is moved from chamber-to-chamber during operation. In general, such a device includes a first narrow channel arrangement extending between, and in communication with, the first and second chambers, and a second channel arrangement extending between, and in communication with, the second and the third chambers. The transport mechanism generally provides for movement of the sample between adjacent chambers.

For typical applications, the pressure in the first chamber is maintained greater than the pressure in the second chamber. The pressure in the third chamber is typically lowest, to facilitate the analysis conducted therein.

Generally, a surface to be tested is prepared on a substrate film which is threaded between the first and second isolated regions by passage through the narrow channel. Surface preparation may be conducted, for example, by: deposition of a thin film onto the substrate film; by surface modification of the substrate film; by modification of a surface film previously deposited on the substrate film; or by similar methods. For preferred embodiments two narrow channels between the first and second regions are provided, so that the substrate film can be threaded first from the first region into the second region, and then back from the second region to the first region. A two channel arrangement, similarly operable, is preferably provided between first and second chambers of a multi-chamber first region.

In preferred applications, the surface to be tested is prepared on an elongate flexible substrate film. The film is threaded from the first chamber, through the second chamber and into the third chamber. At the interface between each pair of adjacent chambers, the film is passed into an arrangement, comprising the previously described elongate channels, which acts as a seal between chambers. In general, the interface between each adjacent pair of chambers comprises an elongate slot through which the film is threaded. The slot acts as an environmental a seal, when adjacent chambers are differentially pumped. For example, in a preferred embodiment comprising three chambers, the first chamber, in which the sample is generated, may be maintained anywhere from about 300 millitorr up to 1.0 torr, with the next adjacent chamber maintained at $5 \times 10^{-5}$ torr, through differential pumping. The third chamber, comprising the analytical chamber, may for example be maintained at about $5 \times 10^{-6}$ torr, with little difficulty.

It will be understood that the listed pressures are exemplary only, and not limiting.

In a preferred embodiment, an arrangement is provided including a continuous film or strip of substrate, fed from the first chamber, through the second, into the third chamber and then back to the first chamber. A continuous sample strip provides numerous advantages, relating generally to the following:

1. Sample analysis, at the analytical device, may be run within a relatively short period of time after sample generation, in a previous chamber. Further, transport to the analytical device may occur with reasonably low probability of damage to the sample.

2. The continuous strip ensures that as a portion is tested in chamber 3, a portion is held waiting in chamber 2 for analysis. That portion held in chamber 2 is isolated from the conditions of chamber 1, and thus contamination problems are minimized.

3. Analytical testing can be conducted at various points on the sample surface, as a sample surface is moved past the analytic probe. Thus, an averaging effect can be obtained, rather readily. Further, affects from damage to the sample surface, by the analytic probe, are minimized, especially if a short analysis time is used. Sample generation and testing procedures can be developed such that a relatively constant, or other selected and precisely controlled, length of time can be maintained between sample generation, and sample testing. This facilitates consistency of results and good analysis. Also, the relatively convenient system developed lends itself well toward computer control.

4. The need for ultra-high vacuum ($1 \times 10^{-10}$ torr) is generally relaxed. A reason for this, as previously suggested, is that the sample is rapidly isolated from the first chamber and potential contaminants therein, after formation. Thus, ultra-high vacuum, to inhibit contamination, may not be necessary.

5. This system also allows study of processes conducted or pressures greater than those considered acceptable for traditional surface analysis techniques. The reasons for this are, again, that separation and isolation of sample preparation from sample analysis enable such studies.

The continuous strip or substrate film may comprise a continual loop of material, so that the same substrate film is continually recycled throughout the process; or, it may comprise an elongate ribbon fed between supply and take-up rolls positioned in the first region. Arrangements facilitating these two possibilities, are described in detail below.

The drawings constitute a part of this specification and include exemplary embodiments of the present invention, while illustrating various objects and features thereof. It will be understood that in some instances relative component sizes, and material thicknesses, may be shown exaggerated to facilitate and understanding of the invention to those skilled in the art.

BRIEF DESCRIPTION OF THE DRAWINGS

FIG. 2 is a fragmentary schematic side elevational view of the arrangement shown in FIG. 1, with a top cover for the device illustrated exploded therefrom and with portions broken away to show internal detail.

FIG. 3 is a fragmentary cross-sectional view taken generally along line 3—3, FIG. 2, with phantom lines indicating portions out of view; FIG. 3 generally being of a portion of the device operating to selectively orient an extension of a film.

FIG. 4 is a exploded perspective view of a portion of the device shown in FIG. 1.

FIG. 5 is a exploded perspective view of a portion of the device shown in FIG. 1.

FIG. 6 is an end elevational view taken generally from the perspective of line 6—6, FIG. 5.

FIG. 7 is an enlarged, fragmentary, cross-sectional view of a portion of the arrangement shown in FIG. 2.

DETAILED DESCRIPTION OF THE INVENTION

As required, detailed embodiments of the present invention are disclosed herein; however, it is to be understood that the disclosed embodiments are merely exemplary in the invention which may be embodied in various forms. Therefore, specific structural, functional and process details disclosed herein are not to be interpreted as limiting; but rather should be considered as a basis for the claims and as a representative basis for teaching one skilled in the art to variously employ the present invention in virtually any appropriately detailed structure.

The present invention concerns a method and apparatus facilitating conduction of surface studies and characterizations. Through application of the invention, a thin film or surface to be studied is prepared on a substrate. The substrate is moved from a region of the device wherein the surface is generated and/or reacted, to a region of the device wherein the surface may be tested or examined by a variety of analytical methods, including Auger electron spectroscopy (AES), X-Ray photoelectron spectroscopy (XPS), secondary ion mass spectroscopy (SIMS), and ion scattering spectroscopy (ISS). It will be understood that arrangements and methods according to the present invention may be used in application with a variety of analytical techniques, including ones not listed and ones yet to be developed.

Figure 1:
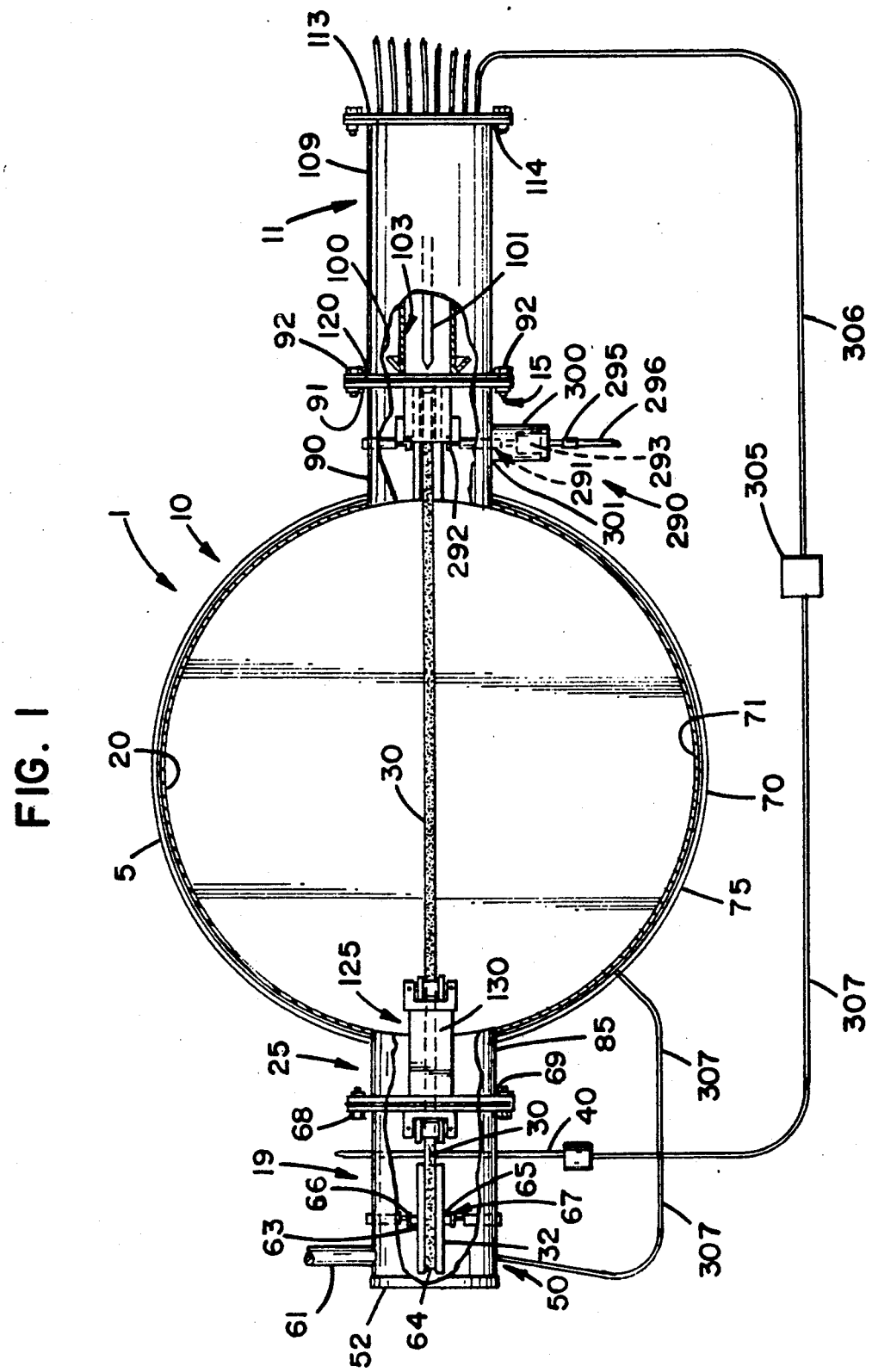
FIG. 1 is a fragmentary schematic top plan view of a portion of a device according to the present invention, having a cover removed therefrom rendering certain internal portions viewable; and, having portions broken away to show internal features.

The reference numeral 1, FIGS. 1 and 2, generally designates a device or assembly according to the present invention. In FIG. 1, a partially schematic representation of an assembly 1 depicted, in top elevational, with a cover over a central portion removed, for viewing of internal parts. It is also noted that certain portions are broken away, to show internal detail. In FIG. 2, a side elevational view of assembly 1 is depicted, with a cover portion 4 shown in an exploded manner.

Referring to FIG. 1, the assembly 1 comprises an enclosure 5 defining first and second regions comprising a sample generation/preparation region 10, and an adjacent sample testing/evaluation region 11. In general, the generation/preparation region 10 comprises a portion of the assembly 1 constructed and arranged for preparation of a sample therein, by preparation of a carrier substrate film, for testing. The testing/evaluation region 11, generally comprises a region construed and arranged for receipt of an analytical tool probe or the like therein, for analyzing a sample.

A seal means or interface between the two regions 10 and 11 is generally indicated at 15. Typically, a pressure deferential exists across interface 15. That is, generally the two regions are maintained under different pressures, and most typically a substantially lower pressure for region 11 is desirable, to inhibit interference with surface analysis and to facilitate operation of the analytical probe. Details concerning this will become more apparent, from the further descriptions.

For the preferred embodiment, the generation/preparation region 10 includes first and second substantially isolated chambers or volumes, 19 and 20 respectively. Chamber 19 comprises a portion of the assembly 1 wherein initial, typically relatively high pressure, steps in preparation of a selected chemical film or sample surface on or of a substrate film can be selectively conducted if desired. Chamber 20, comprises a second volume in which reactions can be conducted at the sample or film surface, if desired. For example, chamber 20 might be selectively filled with a gas which it is desired to have reacted with the film of material generated in chamber 19. Even if no follow-up reactions are conducted in chamber 20, the chamber 20 provides a region to which a prepared sample from chamber 19 may be removed, for protection from the environment of chamber 19, while awaiting transfer to region 11 for analysis. In some instances, initial sample preparation steps could be conducted in chamber 20.

The interface between chambers 19 and 20 is generally indicated at 25; and for many typical operations chambers 19 and 20 will be maintained under a pressure differential, by interface means described below.

Referring to FIG. 2, for the preferred embodiment a continuous strip or substrate 30 is provided as the substrate for carrying a thin film or chemical surface to be analyzed. The substrate 30 comprises a loop 31 mounted to extend around mounting roller 32 and wheel or pulley 33. Thus, referring to FIG. 2, continuous strip or substrate 30 may be viewed as extending from chamber 19, through chamber 20, through interface 15, to region 11, back through chamber 20, and back into chamber 19. Rotation of either of roller 32 or pulley 33 drives strip 30 through a rotation cycle. While the loop 31 may be driven in either direction, for reasons indicated below preferably it is driven as shown by arrows 34, for the embodiment shown.

For the preferred embodiment strip or substrate 30 includes one 180° twist therein, for example as indicated at 35. Thus, strip 30 is similar to a Mobius strip. Advantages obtained from this will be apparent from further descriptions below. Preferably the twist 35 is positioned in the second chamber between interface 25 and interface 15.

The substrate 30 may be manufactured from a variety of substrate materials. Generally what is required is a relatively strong, flexible, film or ribbon, for example a polyamide film (Kapton ®, DuPont), a polyester film, a stainless steel film or the like. A variety of sizes of substrates may be utilized in arrangements according to the present invention. For the embodiment illustrated, generally the substrate 30 is about ½ inch (1.27 cm) wide and about 1–4 mils (0.002–0.01 cm) thick. Such a strip is generally sufficiently strong to withstand tensions during use and operation.

During operation, in chamber 19 a first step in preparing a film surface to be tested can be conducted. A variety of techniques may be utilized to prepare the film surface. For example, evaporation techniques, sputtering techniques, glow discharge, electron beam treatments or the like are all applicable. Referring to FIGS. 1 and 2, for the example depicted a sputtering electrode 40 is shown projecting into chamber 19, an approximately equal distance between upper and lower sections 42 and 43 of substrate 30. During operation, the sputtering electrode 40 may be utilized, in a conventional manner, to sputter deposit cathode material on inside surfaces 45, of substrate 30. In this manner a thin layer of material such as copper, aluminum or the like can be applied to the substrate 30. This layer of material can be further treated, or even reacted with other substances, for example either in chamber 19 or chamber 20, to provide a variety of selected coatings or surface films on substrate 30, for analysis. This will be understood further, from other details and the examples reported below.

Still referring to FIGS. 1 and 2, further detail concerning chamber 19 may be understood. In general, methods of applying surface coatings to substrate 30, especially when by means of a sputtering electrode or the like, are conducted under conditions of controlled, and typically reduced, pressure; for example pressures on the order of about $5 \times 10^{-1}$ torr to $1 \times 10^{-4}$ torr. Thus, preferably, chamber 19 is a vacuum chamber 50. Referring to FIG. 2, generally vacuum chamber 50 includes a sidewall 51 and an end cover 52. A variety of arrangements may be utilized for end cover 52, including those of conventional design. Generally, end cover 52 comprises a sealable member 54 which can be provided in sealing engagement with an otherwise open end 60 of the chamber 50. A vacuum pump mechanism in communication via line 61, FIG. 1, temperature control means, gas inlets and outlets, viewing ports, access ports, and similar devices and arrangements, not shown, can be provided in operative association with chamber 50. Such devices and arrangements may be utilized to facilitate and/or monitor, processes undertaken in vacuum chamber 50. Also, devices usable to create, or modify, a layer or film of material to be studied can be provided.

Referring to FIG. 1, generally, roller 32 comprises a circular wheel 63 having a outer periphery with a central, recessed, track 64 therein for receipt of substrate 30. The recessed track 64 ensures that substrate 30 will remain in position on roller 32, and will generally be oriented appropriately. Wheel 63 includes a central hub 65, by which the wheel 63 is mounted upon bearing structures 66 and 67. While a variety of arrangements are possible, for a typical embodiment wheel 63 is an idler wheel, that is it is not directly driven, but rather it rotates freely on bearing structures 66 and 67.

Chamber 50 is mounted in assembly 1 by means of flange 68, in a conventional manner. That is, generally a remainder of the assembly 1 includes a mating flange 69. Attachment may be by means of bolts or the like.

Chamber 20, for the arrangement of FIGS. 1 and 2, comprises a large circular reaction chamber 70 having an internal volume 71, through which substrate 30 passes, on its way from chamber 19 to the testing/evaluation region 11. For preferred embodiments, means are provided such that the environment of volume 71 can be controlled by an operator, especially with respect to internal pressure, temperature, and atmosphere content. Means can also be provided to effect reactions on, or of, surfaces generated in chamber 19. Further, means may be provided to originate or modify a test surface in chamber 20. Still referring to FIG. 1, generally chamber 70 has a circular outer wall 75. Such a shape facilitates construction with little problem of maintenance of a desired level of vacuum therein.

Referring to FIG. 2, chamber 70 includes a removable bottom plate 76, and a removable upper plate 77, generally comprising cover 4. Preferably plate 77 is easily removable, to allow access to the internal volume 71. An L-seal 78, can be provided in a conventional manner to ensure a desired amount of sealing against leakage into volume 71, during use. Plate 76 is similarly sealed and is removable. A view of this is shown in FIG. 7.

Still referring to FIG. 2, reference numeral 80 generally indicates pump means and atmosphere control devices which may be utilized to provide a controlled pressure and atmosphere content, to internal volume 71, during use. Chamber 70 could be provided with a variety of other means, including valve mechanisms, temperature control mechanisms, monitoring devices, viewing ports, and externally operated manipulation devices, in order to maintain a selected environment for substrate 30, as it passes therethrough.

Referring again to FIG. 1, chamber 70 includes thereon a first extension 85 for mounting in internal communication with chamber 19. Extension 85 includes flange 69 thereon, to facilitate such mounting.

Generally oppositely oriented from extension 85, chamber 70 includes a second extension 90, which provides for internal communication with region 11. Extension 90 includes mounting flange 91 thereon, which provides for mounting at interface 15, by bolts 92. Pulley 33, FIG. 2, is mounted in extension 90, preferably in a manner as described below.

Referring again to FIG. 1, generally the testing-/evaluation region 11 is defined by a chamber 100 having received therein an appropriate means, tool, or mechanism for conducting a desired analytical or characterization test. For example, in FIG. 1 a probe 101 of an Auger spectroscopy system 103 is schematically indicated. The probe 101 is oriented, or is adjustably orientable, in an appropriate position relative to a section 105 of substrate 30, for analysis thereof, FIG. 6. Auger spectrometer system 103 could be removed and replaced by a different system, is desired.

Referring to FIG. 2, a purpose of twist 35 in substrate 30 will now be understood. Generally, electrode 40 would be operated to apply a thin film or coating to substrate 30, on inside 45 thereof. To expose the film at side 45 to probe 101, it is necessary to turn the film over, i.e. put a twist therein of 180°. This is accomplished by twist 35. Movement of loop 31 in the direction of arrows 34 ensures the sample not contact roller 32 before it is examined by probe 101.

Generally, chamber 100, FIG. 1, includes an inner volume in which temperature, pressure and atmosphere can be readily controlled. Most preferably chamber 100 is a circular vacuum chamber 109 provided with control means such as a pump mechanism 110, FIG. 2, suitable for providing a high operating vacuum in chamber 100. Temperature control means, gas inlet and outlet lines, monitoring devices, and electrical and mechanical devices for operation of Auger spectrometer system 103, not shown, may also be provided in chamber 100. Access to an internal portion of chamber 100 can be provided by means of a cover plate 113, on an end flange 114. Generally, chamber 100 may be mounted in assembly 1, by means of a mounting flange 120, and bolts 92, in engagement with flange 91. It will be understood that suitable seal means, to protect internal, generally low pressure, environments can be provided in a conventional manner. W 123 provide for communication with internally received analytical devices.

In many typical operations, the environments of the three chambers 19, 20 and 100 will be substantially different. In particular, different pressures often may have to be maintained of the three chambers. For example, for many foreseen operations typical operating pressures for chamber 19 will be on the order of $5 \times 10^{-1}$ torr to $1 \times 10^{-4}$ torr; pressures for reaction chamber 70 would typically be on the order of one two-thousandth of this, i.e. between about $2 \times 10^{-3}$ torr to $5 \times 10^{-8}$ torr; and, typical pressures for an analytical chamber 100 are on the order of $5 \times 10^{-8}$ torr to $5 \times 10^{-10}$ torr. The different pressures will typically be provided by independent pumps, however alternate arrangements may be used.

It is noted, however, that the free passage of continuous loop 31 of substrate 30 among and/or between the various chambers, is desired. That is, substrate 30, having a surface to be examined should be transported between chambers without: exposure to the environment; potential damaging contact with various materials including components of the assembly 1; and, exposure to undesired elements. This is accomplished by means of differentially pumped seals at each of interfaces 15 and 25.

While the interfaces 15 and 25 operate substantially similarly, for the preferred embodiment they are structured somewhat differently, as indicated below. The seal at interface 25 is indicated generally in FIG. 4; and, the seal at interface at 15 is indicated generally in FIGS. 5 and 6.

Referring to FIGS. 1 and 4, at interface 25, substrate 30 passes through differential seal or assembly 125. In particular, a transport channel arrangement is provided. Seal 125 includes a central block 126 having upper and lower troughs or transport channels 127 and 128 therein, and first and second opposite covers 130 and 131. In general, trough 127 extends along and completely across an upper surface 133 of block 126. Trough 127 is sized to receive substrate 30 extending therethrough. Trough 127 is enclosed by cover plate 130, mounted for example by bolts not shown, to form an enclosed transport channel 134 extending between and in communication with chambers 19 and 20.

Similarly, trough 128, in surface 140 of block 126, extends completely thereacross, and is sized for receipt of substrate 30 therethrough. Trough 128 is enclosed, by means of cover plate 131 and bolts not shown, to form a second transport channel 143 extending between and in communication with chambers 19 and 20.

Referring to FIG. 2, block 126, with covers 130 and 131 thereon, extends across the interface 25 between chambers 19 and 20. As the substrate 30 extends through the elongate channels 134 and 143, the substrate 30 is moved between isolated regions in which different pressures or atmospheres may be maintained. That is, the elongate, narrow, channels 134 and 143 facilitate the differentially pumped seal system. In particular, chambers 19 and 20 can be pumped, by a vacuum pump means, such that the two chambers have different pressures, and the different pressures are maintained due to a slow rate of transport of gas which will occur along and through the elongate and relatively narrow troughs 127 and 128.

Still referring to FIG. 4, the remainder of the assembly depicted in FIG. 4 concerns: means providing for secure, sealing, mounting of the differential seal or assembly 125 within the overall assembly 1; and, means facilitating control of the positioning of the substrate 30, relative to channels 134 and 143.

In FIG. 4, a mounting plate 145 for assembly 125 is depicted. Mounting plate 145 includes upper and lower slots 147 and 148 therethrough appropriately sized to be overlapable with ends of channels 134 and 143, for extension of substrate 30 therethrough. Plate 145 also includes mounting apertures or slots 150 and 151 therein. Slots 150 and 151 are alignable with bores 153 and 154 in block 126. By means of bolts 155 and 156, plate 145 can be mounted. Slotted shapes to apertures 150 and 151 permit plate 145 to selectively be slid vertically, relative to bores 153 and 154, to facilitate a desired alignment between slots 147 and 148, and channels 134 and 143.

Plate 145 includes an outer periphery 160, with an o-ring type seal 161 thereon. Referring to FIG. 2, it will be understood that plate 145 can be positioned within chamber sidewall 51, such that seal 161 provides a seal therebetween. Positioning can be maintained by means of set screws (now shown), or the like, which can extend through apertures 162 provided in an outer skirt 163.

For the preferred embodiment, and as illustrated in FIG. 4, guide means are provided at opposite ends of the assembly 125/mounting plate 145 combination, to facilitate appropriate directing of substrate 30 through the troughs 127 and 128. In particular, first and second guide blocks or mechanisms 165 and 166 are depicted, FIG. 4. It will be understood that guide blocks 165 and 166 can be substantially identical to one another, but mounted in opposite manners.

Referring to FIG. 3, operation of guide block 166 will be understood. In particular, substrate 30 is viewable passing through channels 134 and 143. The guide block 166 includes a pair of guide rollers, i.e. upper and lower guide rollers 170 and 171. The rollers 170 and 171 are adjustable in orientation, so that they can be brought into contact with substrate 30 in a manner assuring that the substrate 30 will pass smoothly through channels 134 and 143, without contacting walls thereof. Thus, rollers 170 and 171 are basically idler./guide rollers to facilitate directioning of the substrate 30. Further detail concerning guide blocks 165 and 166 will be understood by reference to FIG. 4, as follows:

In FIG. 4 guide block 165 is shown in an exploded perspective manner. Guide block 165 includes a mounting block 175 and upper and lower guide rollers 176 and 177. Upper roller 176 is mounted in a channel 180 in block 175 by means of axle pins 182 and 183, which mate with bearings, not shown, in rollers 176 and 177. The axle pins 182 and 183 are axially adjustable within channels 185 and 186, to permit lateral adjustment of the positioning of roller 176. Anchor screws or set screws 188 and 189 retain pins 182 and 183 in a selected orientation. Similarly, bottom roller 177 is mounted by means of pins 190 and 191, and anchor screws 192 and 193. It is noted that each of rollers 176 and 177 includes a central recessed race, 195 and 196 respectively, therein to facilitate guidance of elongate substrate 30.

By the mechanism just described, both of rollers 176 and 177 are laterally adjustable, by means of a set screws and pins, within block 175. Generally a vertical distance between the rollers 176 and 177 is maintained constant, since the channels 134 and 143 are maintained a constant separation from one another. However, vertical positioning of block 175 is important, to ensure that the opposite rollers 176 and 177 operate to maintain the substrate 30 suspended within channels 134 and 143, and not brushing one of the channel walls. In general, block 175 is mountable by means of bolts 155 and 156. Slotted apertures in the block 175, not viewable in FIG. 4, facilitate vertical movement. This will be better understood by referring to that portion of FIG. 4 in which block 166 is illustrated, with analogous slotted apertures.

In particular, referring to guide block 166, FIG. 4, a block 200 is viewable mounted by means of bolts 201 and 202. Block 200 includes a central vertical channel 205, and first and second rollers 203 and 204, FIG. 3. Block 200 is mountable by means of slotted apertures or slots 209 and 210, which are vertically aligned to permit vertical adjustment. Slots 211 and 212 extend channels 134 and 143 respectively. Similarly, slots in block 175 extend channels 134 and 143.

Again, from an examination of FIGS. 2 and 3, it will be apparent that guide block mechanisms 165 and 166 generally operate as a positioning mechanism to maintain substrate 30 suspended for passage through channels 134 and 143, without likely damaging contact with walls of the channels 134 and 143. It is noted that the substrate 30 will contact the idler rollers or guide rollers of each of guide block mechanisms 165 and 166. However, it has been observed that generally this has not involved sufficient damage to films on the substrate 30, to be a problem. Further, it is noted that at least during an initial passage outwardly from chamber 19 into chamber 20, that side of the substrate 30 which contacts rollers of the guide mechanisms, is a side opposite from that on which the surface to be studied is generated. Thus, if only one revolution of substrate 30 is used after film generation, only a "backside" of the substrate contracts the idler rollers.

Referring to FIG. 2, at interface 15 a differentially pumped seal system is also provided. As the substrate 30 is passed through the interface 15, section or portion 105 thereof is brought into alignment with probe 101. This seal system is illustrated in detail in FIGS. 5 and 6.

Referring to FIG. 5, the seal system at interface 15 comprises a pulley and a block arrangement 215 which define a transport channel arrangement and which include wheel 33 mounted therein. Wheel 33 includes an outer peripheral area 220 having a race 221 therein, sized for receipt of substrate 30. For the preferred embodiment depicted race 221 is recessed considerably. Arrangement 215 also includes a block 225, for mounting wheel 33. Block 225 includes a mounting channel 229, for receipt of a portion of wheel 33 therein. For the preferred embodiment depicted mounting channel 229 includes central roll cups 230 and 231. When wheel 33 is received within channel 29, roll cups 230 and 231 extend partially into race 221. Thus, in the area of each of roll cups 230 and 231, an elongate, narrow, slotted passageway or transport channel is formed between portions of the block 225 and portions of the wheel 33. During use, the substrate 30 extends through these passageways. Due to the passageway's elongate, narrow, shape, a differential seal is formed at interface 15, between chambers 20 and 100. As a result, the chambers can be pumped to different pressures, as previously indicated. Roll cups 230 and 231 are formed curved, to draw out the channels formed thereby around a substantial portion of wheel 33.

For the preferred embodiment shown, the pulley and block arrangement comprises a wheel 33 having a recessed race 221, and a block 225 having a channel 229 with roll cups 230 and 231 therein. It will be understood that a variety of alternate arrangements may be provided. For example, a wheel without a recess, and a block having a channel but no roll cups, could be provided in a manner which yields a narrow slot or seal for passage of the substrate 30 therethrough. Further, there is no particular reason why race 221 needs to be flat and cross-section, rather for some embodiments a curved or otherwise shaped race may be used.

The mechanism for mounting pulley 33 will also be apparent from examination of FIG. 5. In particular, pulley 33 is mounted upon mounting pin or axle 235. If desired, a nonslip association between pulley 33 and axle 235 can be provided, so that when axle 235 is rotated, pulley 33 is driven. Axle 235 is mounted within opposite slots 236 and 237, to extend between opposite mounting blocks 240 and 241. Block 240 is mounted by means of bolts 243 and 244 extending through slots 245 and 246. The elongate shape of slots 245 and 246 comprises a lateral adjustment mechanism which permits adjustment in horizontal position of block 240, upon block 225. Similarly, block 241 is mounted by means of bolts 250 and 251 extending through slots 252 and 253.

Horizontal adjustment of pulley 33 may be important, in order to properly position race 221 relative to probe 101, FIG. 2, to focus the analytical probe 101. This facilitates focus after a probe change, or probe maintenance. Adjustment can be accomplished by means of adjustment screws or set screws 255, 256, 257 and 258, which bear against an outer rim 260 of block 225.

Block 225, for the embodiment shown, comprises a machined member including lateral semicircular flanges 265 and 266 thereon. To these are mounted plate 270, FIG. 6. Plate 270 includes a central slot 275 therein, which exposes portion 105 of substrate 30 in race 221, shown in phantom lines. Portion 105 is that portion of substrate 30 which is exposed to the probe 101, FIG. 1. Slot 275 generally provides an opening or extension of chamber 100 into interface 15. Along an outer peripheral area 277 of the plate 270/block 225 combination, FIG. 5, an o-ring seal 278 or the like may be positioned, to facilitate sealing at interface 15.

Referring still to FIGS. 2 and 5, it is readily apparent that arrangement or mechanism 215 operating at interface 15 can be used to guide the strip of substrate 30 into slot or area 275, FIG. 6, for testing. Selected horizontal positioning of pulley 33 can be used to adjust the space between the tip of probe 101 and section 105, which generally should be on the order of about 0.3 inches (0.76 cm), for typical operation of the selected Auger spectrometer probe 101.

A variety of means may be utilized to "drive" the system. That is, various mechanisms, including conventional ones, may be utilized to drive one or the other of roller 32 and pulley 33, FIG. 2, in order to move substrate 30. Thus, a transport mechanism is provided to move a test sample between isolated regions. For the embodiment shown, pulley 33 is the powered or driven wheel. In particular, referring to FIG. 5, axle pin 235 includes an extension 282 thereon (shown fragmented) which extends laterally from the system and is engagable by a drive mechanism 290, FIG. 1. Typically, rotational motion of axle pin 235 is facilitated by mounting in bearings, not shown. Such bearings would generally be retained by blocks 240 and 241, FIG. 5. Generally, it will be understood, drive mechanisms which do not substantially inhibit operation of the analytical device will be preferred. Thus it may be necessary to provide a drive mechanism which includes means inhibiting magnetic or electrical interference with sensitive instrumentation. Again referring to FIG. 1, the drive mechanism 290 depicted comprises a double universal joint 291 coupled to pulley 33 at bearing 292. The double universal joint 291 is coupled to a ferrofluidic rotary seal 293, and then to a coupling joint 295. The system is driven by shaft 296 in a conventional manner. It is noted that drive mechanism 290 is not depicted in FIG. 2, so that other portions of the apparatus are not blocked from view. Preferably a tachometer controlled D.C. motor, not shown, or a computer controlled stepper motor, not shown, are used. Threaded sealing boss 300 welded to the chamber wall at joint 301 accepts the rotary seal 243.

A variety of control means, not shown, may be utilized in association with the device of FIGS. 1 through 5. Computer control means may be utilized, for example, to provide for a desired programming of substrate movement and/or sample analysis. In some instances it may be desirable to move the substrate at a constant rate, for a selected distance, then pause same during a test, then again move the substrate for a selected distance at a selected rate. In some studies it may be desirable to take a plurality of data points at selected time intervals or for a selected time interval, and then to increase the time interval by a selected amount. These, and a variety of other programs, may be easily generated by means of computer systems, or the like, interfaced with control means for the assembly 1.

Figure 8:
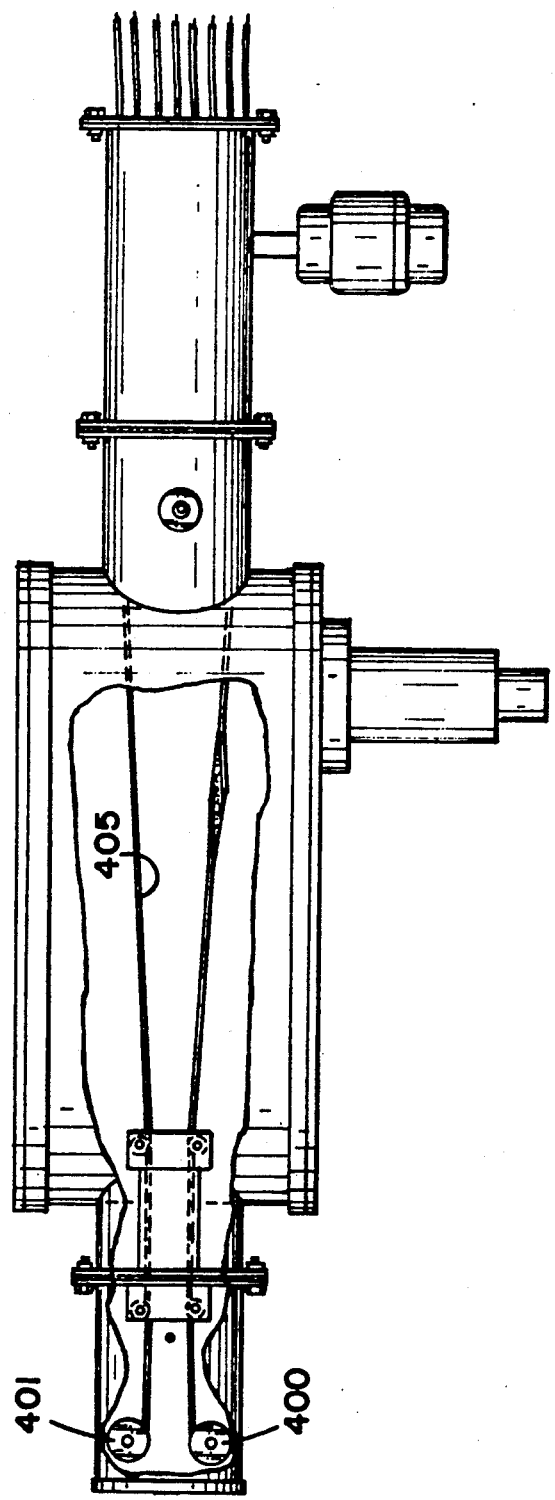
FIG. 8 is a fragmentary, schematic, side elevational view of an alternate embodiment of the invention.

In general, the assembly or apparatus 1 illustrated in FIGS. 1 through 6 utilizes a continuous loop. In some arrangements it may be desirable to utilize an elongate, substantially continuous, thread of substrate, not formed as continuous loop. An example of such an arrangement is illustrated in FIG. 8, wherein feed out and take-up rollers, wheels or reels 400 and 401 are shown with substrate 405 extending therebetween. In other aspects, the apparatus of FIG. 8 may be substantially identical to the apparatus of FIGS. 1 through 7, although it may be desired to power take-up roller 401 rather than a pulley of the pulley and channel block system, for such an arrangement.

Operation of an assembly according to the above-referenced invention, and advantages derived therefrom, will be even more apparent from the following reported examples. It is noted that for preferred operation, all bearing surfaces should be either substantially oil-free or lubricated with a vacuum compatible oil, such as Tovr Lube © available from Sputtered Films, Inc.

EXAMPLE 1

Reactive sputter deposition is a process whereby metal compounds, for example copper oxide, are deposited on a substrate. A reactive gas, such as oxygen, is blended with the neutral sputtering gas, for example Argon, to form the oxide as the metal deposit is generated by the sputtering electrode. Control of the ratio of metal to reacting gas is very difficult to achieve in conventional processes. However, with the techniques of the present invention such control is readily obtained, as indicated by the following.

An apparatus generally corresponding to FIGS. 1 through 6 was prepared. The device was driven by a speed-controlled D.C. motor at a substrate surface velocity of approximately 2 feet per minute. A magnetron sputtering target of copper was deployed in the first chamber (chamber 19) and was operated at 120 watts D.C., unless otherwise indicated, and at an Argon pressure of $2\times10^{-2}$ torr, unless otherwise indicated. The analysis chamber, chamber 100, was fitted with a commercial Auger electron spectrometer and was controlled by computer.

The copper oxide was deposited in the first chamber and the sample was transported through the second chamber to the third chamber, for analysis. The atom ratio of copper to oxygen was calculated from the obtained spectra, and was compared to a preselected value of 2.0. Deviation in composition was minimized by computer adjustment of oxygen bleed into the Argon atmosphere in the first chamber.

As process parameters were varied, the following results were obtained. A decrease in sputtering power to 80 watts caused a momentary increase in oxygen content, but the apparatus and technique allowed for an immediate decrease in the oxygen flow, to return the stoichiometry to a value of 2.0. Decreasing argon pressure in the first chamber, caused the oxygen content to increase momentarily, but again the apparatus and technique provided for correction of the stoichiometry to a value of 2.0. This experiment successfully demonstrated the utility of the technique and apparatus, in process control of the preparation of thin films. In particular, the analytical technique was used in coordination with the film preparation technique in a preferred manner for continual monitoring and control, with relatively low error.

EXAMPLE 2

Techniques according to the present invention may be used to study and establish the mechanism and kinetics of some chemical reactions on surfaces, for example electron induced decomposition of copper oxide. For this example, a previously deposited film of copper oxide was exposed to an electron beam. Both the time of exposure, and fluence of the beam, were varied. The rate of loss of $O_2$ was measured by Auger spectroscopy. If a threshold value for time and/or fluence was observed, it could be concluded that the desorption process is thermally controlled, and is not initiated by excited-state phenomena.

An apparatus according to FIGS. 1 through 6 was fitted with a digital stepper motor to drive the belt. The stepper motor was driven by the same computer that operated the Auger electron spectrometer in the analysis chamber. In carrying out the experiment the stepper motor was advanced a step (about 0.5 mm movement of substrate per step) and then, after a preselected wait time during which the electron beam in the Auger electron spectrometer irradiated the sample surface, the point was analyzed. Each data point in the spectrum was collected from a new spot as a result of the step-wait-analyze procedure. Once an entire spectrum was collected, the wait time was increased and a new spectrum was collected. The data were collected at four different electron beam current settings, at identical beam voltages.

The results indicated that there was a threshold current below which there was no observable decomposition of the copper oxide. Also, the decomposition rate was exponential with the electron beam dosage (current). These data indicate that the process is thermally activated and caused by heating in the electron beam. Decomposition by an excited electronic state mechanism would have been linear with electron beam current, and would have had no minimum threshold of exposure.

EXAMPLE 3

An apparatus according to FIGS. 1-6 was prepared as described in Example 2. To study kinetics, the middle chamber was fitted with a resistive evaporator which was used to coat the belt with copper phthalocyanine (CuPc), a metalloorganic pigment which is commercially available. Once the belt was coated in its entirety, as observed by appearance and color, the evaporation was ceased. The composition was monitored continuously during the course of evaporation by the Auger electron spectrometer to establish the quality of the coating.

Since CuPc contains no oxygen in its structure (verified by the analysis during deposition), any oxygen uptake observed in subsequent analysis should be due to oxidation of the CuPc in the presence of the electron beam of the Auger electron spectrometer, in the analysis chamber. The middle chamber and analysis chambers were filled with oxygen to a pressure of $1\times10^{-5}$ torr, and the film was analyzed in a step-wait-analyze fashion, as in the copper oxide decomposition example above. Analogously to Example 2, the wait time was increased after each spectrum. The observed result was that, once again, there was a threshold of exposure dosage below which no oxygen was taken up by the CuPc. There was a near exponential dependence of oxygen uptake with dosage. This indicated a thermally activated process in which the heat is supplied by the electron beam in the Auger electron spectrometer. Visual inspection of the electron irradiated CuPc showed a change in film color from blue to black, where the electron beam irradiated the sample.

Experiments 2 and 3, in addition to having shown the utility of the apparatus and technique in the study of surface reaction kinetics and mechanisms, demonstrate that the apparatus and techniques can be applied to successfully eliminate electron beam damage effects from Auger electron analysis, as long as electron dosage is kept below a threshold of damage. That is, either beam current density or time of sample exposure can easily be kept sufficiently low with an apparatus according to the present invention, to permit analysis without sample damage. Threshold points are easily defined.

It is to be understood that while certain embodiments of the present invention have been illustrated and described, the invention is not to be limited to the specific forms, arrangements of parts, methods or techniques herein described as shown.

What is claimed and desired to be secured by Letters Patent is as follows:

1. An apparatus operable to facilitate preparation and analysis of a layer of material; said apparatus comprising:
   (a) an enclosure defining first and second regions said first region being constructed and arranged for preparation therein of a test layer of material to be analyzed, at a first pressure less than atmospheric pressure; and, said second region being constructed and arranged to operatively receive therein a test layer of material to be analyzed and an analytical tool for conduction of selected analysis at a second pressure less than atmospheric pressure;
   (b) means for maintaining said first region at said first pressure;

(c) means for maintaining said second region at said second pressure, said first and second pressures being non-equal to one another;

(d) a transport mechanism constructed and arranged to transport the test layer of material from said first region to said second region, for analysis; said transport mechanism including an elongate, flexible, substrate extending from said first region to said second region;

(e) seal means substantially isolating said first and second regions from one another; said seal means including an elongate transport channel arrangement including at least one seal means transport channel extending between, and in communication with, said first and second regions; and, (f) said transport mechanism including means for selected movement of said elongate substrate through said seal means transport channel, thereby selectively exposing portions of said substrate, and a test layer of material thereon, to said second region.

2. An apparatus according to claim 1 wherein said second region includes means for conducting Auger spectroscopy analysis of a layer of material transported therein.

3. An apparatus according to claim 1 wherein said first region includes means for deposition of a layer of material on said substrate, through sputtering electrode deposition.

4. An apparatus according to claim 3 wherein said second region includes means for conducting Auger spectroscopy analysis of a layer of material transported therein.

5. An apparatus according to claim 24 including:
(a) interface means dividing said first region into first and second substantially isolated chambers; said second chamber being oriented between said first chamber and said second region;
  (i) said interface means including an elongate narrow channel extending between and in communication with said first and second chambers; said narrow channel being sized for extension of said substrate therethrough; and
  (ii) said substrate extending from said first chamber; through said narrow channel; through said second chamber; to said second region; and, back into said first region.

6. An apparatus according to claim 5 wherein:
(a) said first chamber includes a mounting roller therein; and,
(b) said substrate comprises a continuous loop mounted on said mount roller.

7. An apparatus according to claim 1 wherein:
(a) said seal means includes a pulley and block arrangement;
  (i) a pulley of said pulley and block arrangement having an outer periphery sized for receipt of a portion of said substrate thereagainst;
  (ii) said pulley and block arrangement cooperatively defining first and second narrow transport channels through which said substrate is threaded, during use; each of said first and second narrow transport channels extending between and in communication with, said first and second regions; at least one of said first and second narrow transport channels comprising said seal means transport channel; and (iii) said pulley and block arrangement being positioned at an interface between said first and second regions; said block including a space between said first and second narrow channels in which said pulley outer periphery, and a portion of said substrate received thereon, is exposed to said second region.

8. An apparatus according to claim 7 wherein:
(a) said pulley outer periphery includes a recessed channel therein sized for receipt of a portion of said substrate therein; and,
(b) said block comprises a channel block including roll cups directed into and received by said pulley recessed channel.

9. An apparatus according to claim 8 wherein:
(a) said first region includes a mounting roller therein; and,
(b) said substrate comprises a continuous loop mounted on said mounting roller and said pulley.

10. An apparatus according to claim 9 wherein:
(a) said continuous loop includes a 180° twist therein positioned between said mounting roller and said pulley; and,
(b) said apparatus includes means constructed and arranged to prepare a test layer of material on an inside surface of said substrate along a position between said 180° twist and said mounting roller.

11. An apparatus according to claim 7 wherein:
(a) said first region includes a mounting roller and a take-up roller; and,
(b) said substrate is fed from said mounting roller through said pulley and block arrangement and to said take-up roller.

12. A method for preparing and evaluating a layer of material; said method including the steps of:
(a) providing first and second substantially isolated regions having a narrow transport channel extending therebetween and in communication therewith;
(b) providing an elongate substrate oriented in extension: from said first region; through said narrow transport channel; and, to said second region;
(c) preparing a layer of material to be evaluated on said substrate in said first region; said step of preparing a layer of material to be evaluated being conducted at a first pressure less than atmospheric pressure;
(d) transporting a portion of said elongate substrate, with the layer of material to be evaluated thereon, through said narrow transport channel and into said second region; and,
(e) evaluating the layer of material by an analytical process conducted in the second region and at a second pressure; the second pressure being less than atmospheric and different from the first pressure.

13. The method according to claim 12 including:
(a) providing said elongate substrate in extension back from said second region to said first region; and,
(b) transporting said substrate with the layer of material thereon back into said first region after said step of evaluating.

14. The method according to claim 12 including:
(a) providing, in said first region, first and second chambers substantially isolated from one another; and, interface means including an elongate narrow channel extending between and in communication with said first and second chambers;

(b) providing said elongate substrate in extension: from said first chamber; through said interface means narrow channel; through said second chamber; through said narrow transport channel; and, to said second region; and, (c) conducting at least part of said step of preparing said layer of material to be evaluated in said first chamber.

15. A method according to claim 14 including a step of conducting a modification of the layer of material in said second chamber.

16. A method according to claim 12 including a step of:

(a) adjusting said step of preparing a layer of material to be evaluated in said first region, in response to information obtained by evaluation conducted in said second region.

17. A method according to claim 12 wherein said step of evaluating includes evaluation by Auger spectroscopy.

* * * * *